United States Patent [19]

Amuti

[11] Patent Number: 5,480,856
[45] Date of Patent: Jan. 2, 1996

[54] 1,2,4-TRIAZOLO[1,2-A]PYRIDAZINE-1,3(2H)-DIONE HERBICIDES FOR CITRUS, SUGARCANE, OIL PALM AND THE LIKE

[75] Inventor: Kofi S. Amuti, Wilmington, Del.

[73] Assignee: E. I. Du Pont de Nemours and Company, Wilmington, Del.

[21] Appl. No.: 278,764

[22] Filed: Jul. 22, 1994

Related U.S. Application Data

[63] Continuation of Ser. No. 90,150, Jul. 28, 1993, abandoned, which is a continuation-in-part of Ser. No. 649,355, Feb. 1, 1991, abandoned.

[51] Int. Cl.⁶ .......................... A01N 43/58; A01N 43/653
[52] U.S. Cl. ............................................. 504/236; 504/273
[58] Field of Search ...................... 504/236, 273

References Cited

U.S. PATENT DOCUMENTS

| 4,452,981 | 6/1984 | Nagano et al. | 544/236 |
| 4,881,967 | 11/1989 | Semple | 71/92 |
| 4,925,481 | 5/1990 | Blume et al. | 71/92 |

FOREIGN PATENT DOCUMENTS

| 075267 | 9/1982 | European Pat. Off. . |
| 271170 | 12/1987 | European Pat. Off. . |

*Primary Examiner*—S. Mark Clardy

[57] ABSTRACT

Substituted tetrahydro-1H-[1,2,4]-triazolo[1,2-a]pyridazine-1,3(2H)-dione herbicides of Formula I provide broad spectrum weed control in citrus, sugarcane, coffee, oil palm, grapes and nut trees

6 Claims, No Drawings

1,2,4-TRIAZOLO[1,2-A] PYRIDAZINE-1,3(2H)-DIONE HERBICIDES FOR CITRUS, SUGARCANE, OIL PALM AND THE LIKE

CROSS-REFERENCE TO RELATED APPLICATION

This is a continuation of U.S. application Ser. No. 08/090, 150, filed under 35 USC 371 on Jul. 28, 1993, now abandoned, which is a continuation of PCT/US92/00360, filed Jan. 29, 1992, which is a continuation-in-part of U.S. application Ser. No. 07/649,355, filed Feb. 1, 1991, now abandoned.

BACKGROUND OF THE INVENTION

The compounds of the instant invention are known for use as herbicides. Such disclosure is found in EP-A-075,267 and U.S. Pat. No. 4,881,967. There are, however, no teachings for the use of such herbicides in selected crops such as citrus, sugarcane, coffee, banana, oil palm, loblolly pine, rubber, cocoa, grapes, plantain, pineapple, fruit trees such as apples, nut trees, and turf grass such as Kentucky bluegrass. These crops are important markets and are cultivated particularly in regions of the Pacific rim and South America. Citrus, turf grass and loblolly pine also are grown elsewhere.

The yields of selected crops such as citrus, sugarcane, coffee, banana, oil palm, loblolly pine, rubber, cocoa, grapes, fruit trees, Kentucky bluegrass, and Bermudagrass tend to be lessened by undesired plants such as crabgrass, guineagrass, itchgrass and the like. In addition, the yields of these crops tend to be reduced by crop plants such as corn, cotton, wheat, rice, and the like. A need therefore exists for controlling these types of plantings to improve the yields of selected crops such as those mentioned above.

SUMMARY OF THE INVENTION

This invention comprises the use of the compound of Formula I

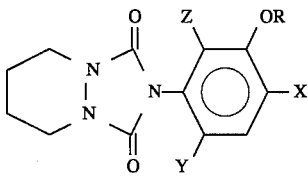

wherein
R is isopropyl, allyl, propargyl or —CH(CH$_3$)C≡CH;
X is Cl or Br;
Y is F or Cl;
Z is H or can be taken together with R as

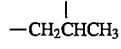

such that the linking oxygen is attached to the methine carbon;
and its agriculturally suitable salts for broad spectrum weed control in selected crops such as citrus, sugarcane, coffee, banana, oil palm, loblolly pine, rubber, cocoa, grapes, plantain, pineapple, fruit trees such as apples, nut trees, turf grass such as Kentucky bluegrass, and the like.

Preferred for reasons of more efficient weed control and/or better crop tolerance, the method of the invention for controlling undesired plantings in selected crops such as, citrus, sugarcane, coffee, banana, oil palm, loblolly pine, rubber, cocoa, grapes, plantain, pineapple, fruit trees such as apples, nut trees, and turf grass such as Kentucky bluegrass and the like comprises applying to the locus of the undesired plantings in these crops a herbicidally effective amount of a compound of Formula I wherein X is Cl, Y is F and Z is H. Preferably, the crop selected is chosen from the group of citrus, sugarcane, coffee, banana, oil palm and loblolly pine. More preferably, the compound of Formula I is either 2-[4-chloro-2-fluoro-5 -[(2-pyropynyl)oxy]-phenyl]tetrahydro-1 H-[1,2,4]-triazolo[1,2-a]pyridazine -1,3(2H)-dione or 2-(7-chloro-5 -fluoro-2,3-dihydro-2-methyl-4-benzofuranyl)tetrahydro-1H-[1,2,4]triazolo-[1,2-a]pyridazine-1,3(2H)-dione.

DETAILED DESCRIPTION OF THE INVENTION

Having briefly summarized the invention, the invention will now be described in detail by reference to the following specification and non-limiting examples. Unless otherwise specified, all percentages are by weight.

Synthesis

The compounds of Formula I can be prepared according to the procedures of EP-A-075,267 and U.S. Pat. No. 4,881,967, the disclosures of which are herein incorporated by reference.

Particularly important compounds of Formula I for use in this invention include the following:

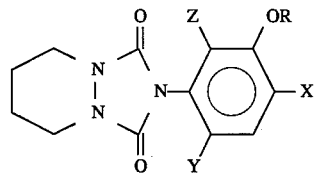

| X  | Y  | Z          | R              |
|----|----|------------|----------------|
| Cl | Cl | H          | —CH$_2$C≡CH    |
| Cl | Cl | H          | —CH$_2$CH=CH$_2$ |
| Cl | Cl | H          | —CH(CH$_3$)C≡CH |
| Cl | Cl | H          | —CH(CH$_3$)$_2$ |
| Cl | Cl | —CH$_2$CHCH$_3$ |            |
| Cl | F  | H          | —CH$_2$C≡CH    |
| Cl | F  | H          | —CH$_2$CH=CH$_2$ |
| Cl | F  | H          | —(CH$_3$)C≡CH  |
| Cl | F  | H          | —CH(CH$_3$)$_2$ |
| Cl | F  | —CH$_2$CHCH$_3$ |            |
| Br | Cl | H          | —CH$_2$C≡CH    |
| Br | Cl | H          | —CH$_2$CH=CH$_2$ |
| Br | Cl | H          | —CH(CH$_3$)C≡CH |
| Br | Cl | H          | —CH(CH$_3$)$_2$ |

-continued

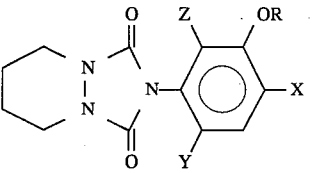

| X | Y | Z | R |
|---|---|---|---|
| Br | Cl | —CH$_2$CHCH$_3$ (with branch) | |
| Br | F | H | —CH$_2$C≡CH |
| Br | F | H | —CH$_2$CH=CH$_2$ |
| Br | F | H | —CH(CH$_3$)C≡CH |
| Br | F | H | —CH(CH$_3$)$_2$ |
| Br | F | —CH$_2$CHCH$_3$ | |

Formulations

Useful formulations of the compounds of Formula I can be prepared in well known forms such as dusts, granules, pellets, solutions, suspensions, emulsions, wettable powders, emulsifiable concentrates and the like.

The methods of making such formulations are well known. Solutions are prepared by simply mixing the ingredients. Fine solid compositions are made by blending and, usually, grinding as in a hammer or fluid energy mill. Suspensions are prepared by wet milling (see, for example, Littler U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux U.S. Pat. No. 3,235,361, Feb. 15, 1966, Col. 6, line 16 through Col. 7, line 19 and Examples 10 through 41;

R. W. Luckenbaugh U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

Many of these forms of the compounds of Formula I may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they typically contain these ingredients in the following approximate proportions:

| Formulation | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emusifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents that may be included in the formulation are described in Watkins, et al., "Handbook of Insecticide Dust Diluents and Carriers", 2nd Ed., Dorland Books, Caldwell, N. J., but other solids, either mined or manufactured, may be used. The more absorptive diluents are preferred for wettable powder formulations and the denser diluents for dust formulations.

Typical liquid diluents and solvents that may be included in the formulations are described in Marsden, "Solvents Guide", 2nd Ed., Interscience, New York, 1950. Solubility of the liquid diluent of under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

In the following examples of the formulation of the compound of Formula I, all parts are by weight unless otherwise indicated.

Example A

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

Example B

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

Example C

| | |
|---|---|
| Wettable Powder of Example B | 5% |
| attapulgite granules (U.S.S. 20–40 mesh; 0.84–0.42 mm) | 95% |

A slurry of wettable powder containing 25% solids is sprayed onto the surface of attapulgite granules in a double-cone blender. The granules are dried and packaged.

Example D

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders and about 3 mm diameter which are cut to produce pellets about 3 mm long. These pellets may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Example E

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

Example F

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 80% |
| wetting agent | 1% |
| crude ligninsulfonate salt (containing (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material then is discharged, screened to the desired size range, generally 14–100 mesh (1410–149 microns), and packaged for use.

Example G

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

Example H

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

Example I

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

Example J

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

Example K

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Example L

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Example M

| | |
|---|---|
| 2-[4-chloro-2-fluoro-5-[(2-propynyl)oxy]phenyl]-tetrahydro-1H-[1,2,4]-triazolo[1,2-a]pyridazine-1,3(2H)-dione | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

The compounds that are employed in the present invention surprisingly are active herbicides for selective and/or general broadleaf and grass weeds control in crops including coffee, cocoa, oil palm, sugarcane, citrus, grapes, fruit trees, nut trees, banana, plantain, rubber, pineapple and loblolly pine.

The compounds of Formula I can be applied as a preemergence or postemergence treatment using techniques such as banding, directed sprays, or broadcast applications. By selecting the appropriate rate which would be apparent to one skilled in the art, the compounds of Formula I can be used in areas where control of vegetation is desired, such as around fuel storage tanks, ammunition depots, industrial storage areas, oil well sites, drive-in theaters, around billboards, highway and railroad structures and in fence rows. Alternatively, by selecting the proper rates, adjuvants and application methods, the compounds of Formula I can be used for selective weed control in plantation crops such as citrus, sugarcane, coffee, oil palm, rubber, cocoa, grapes, fruit trees, pineapple, and turf species such as Kentucky bluegrass. In general, the compounds of this invention are used at 5 to 5000 g/ha with a preferred rate range of 10 to 2000 g/ha rate. One skilled in the art can select the proper rates for a given situation.

The compounds of Formula I also may be used in combination with other herbicides. The compounds of Formula I are particularly useful in combinations with other herbicides for total vegetation control in plantation crops. Examples of other herbicides that may be employed with the compounds of Formula I include, but are not limited to, triazine, triazole, uracil, urea, amide, carbamate, bipyridylium, phenoxy, sulfonylurea and imidazole types, as well as with mefluidide, glyphosate or gluphosinate. Additional examples of herbicides that may be employed with the compounds of Formula I are shown in Table I.

TABLE I

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)-phenoxy]-2-nitrobenzoic acid |
| acrolein | 2-propenal |
| alachlor | 2-chloro-N-(2,6-diethylphenyl)-N-(methoxymethyl)acetamide |
| anilofos | S-4-chloro-N-isopropylcarbaniloyl-methyl-O,O-dimethyl phosphorodithioate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]-carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-N-ethyl-2,6-dinitro-4-(trifluoromethyl)benzenamine |
| bensulfuron methyl | 2-[[[[(4,6-dimethoxy-2-pyrimidinyl)amino]methylcarbonyl]-amino]sulfonyl]methyl]benzoic acid, methyl ester |
| bensulide | O,O-bis(1-methylethyl) S-[2-[(phenylsulfonyl)amino]-ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoro- |

TABLE I-continued

| Common Name | Chemical Name |
|---|---|
| | methyl)phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4 (1H, 3H) pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| CGA 142,464 | 3-(4,6-dimethoxy-1,3,5-triazin-2-yl)-1-[2-(2-methoxyethoxy)-pehnyl-sulfonyl]-urea |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)ethylamino]carbonyl]amino]sulfonyl]benzoic acid, ethyl ester |
| chlormethoxynil | 2,4-dichlorophenyl 4-nitro-3-methoxyphenyl ether |
| chlornitrofen | 2,4,6-trichlorophenyl-4-nitrophenyl ether |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)-imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]phenyl]carbamate |
| desmetryn | 2-(isopropylamino)-4-(methylamino)-6-(methylthio)-s-triazine |
| diallate | S-(2,3-dichloro-2-propenyl)bis(1- |

TABLE I-continued

| Common Name | Chemical Name |
|---|---|
| | methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop | (±)-2-[4-(2,4-dichlorophenoxy)phenoxy]-propanoic acid, methyl ester |
| diethatyl | N-(chloroacetyl)-N-(2,6-diethylphenyl)-glycine |
| difenzoquat | 1,2-dimethyl-3,5-diphenyl-1H-pyrazolium |
| dimepiperate | S-1-methyl-1-phenylethylpiperidine-1-carbothioate |
| dinitramine | $N^3,N^3$-diethyl-2,4-dinitro-6-(trifluoromethyl)-1,3-benzenediamine |
| dinoseb | 2-(1-methylpropyl)-4,6-dinitrophenol |
| diphenamid | N,N-dimethyl-a-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinedium ion |
| diuron | N'-(3,4-dichlorophenyl)-N,N-dimethylurea |
| DNOC | 2-methyl-4,6-dinitrophenol |
| DSMA | disodium malt of MAA |
| dymron | N-(4-methylphenyl)-N'-(1-methyl-1-phenylethyl)urea |
| endothall | 7-oxabicyclo[2.2.1]heptane-2,3-dicarboxylic acid |
| EPTC | S-ethyl dipropylcarbamothioate |
| esprocarb | S-benzyl-N-ethyl-N-(1,2-dimethyl)-propyl)thiolcarbamate |
| ethalfluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl-5-benzofuranyl methanesulfonate |
| Express ® | 2-[[[[N-(4-methoxy-6-methyl-1,3,5-triazine-2-yl)-N-methylamino]-carbonyl]amino]sulfonyl]benzoic acid, methyl ester |
| fenac | 2,3,6-trichlorobenzenacetic acid |
| fenoxaprop | (±)-2-[4-[(6-chloro-2-benzoxazolyl)oxy]-phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)-phenyl]urea |
| fluorochloridone | 3-chloro-4-(chloromethyl)-1-[3-(trifluoromethyl)phenyl]-2-pyrrolidine |
| fluorodifen | p-nitrophenyl a,a,a-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hydrogen (aminocarbonyl)phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| Harmony ® | 3-[[[[(4-methoxy-6-methyl-1,3,5-triazin-2-yl)amino]carbonyl]amino]sulfonyl]-2-thiophenecarboxylic acid, methyl ester |
| hexaflurate | potassium hexafluoroarsenate |
| hexazinone | 3-cyclohexyl-6-(dimethylamino)-1-methyl-1,3,5-triazine-2,4(1H,3H)-dione |
| imazametha- | 6-(4-isopropyl-4-methyl-5-oxo-2- |

TABLE I-continued

| Common Name | Chemical Name |
|---|---|
| benz | imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazole-2-yl]-3-pyridinecarboxylic acid |
| imazaquin | 2-[4,5-dihydro-4-methyl-4-(1-methylethyl)-5-oxo-1H-imidazole-2-yl]-3-quinolinecarboxylic acid |
| imazethapyr | (±)-2-[4,5-dihydro-4-methyl-4-(1-methylethyl)-5-oxo-1H-imidazole-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N'N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]-phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| MON 7200 | S,S-dimethyl-2-(difluoromethyl)-4-(2-methylpropyl)-6-(trifluoromethyl)-3,5-pyridinedicarbothioate |
| mecoprop | (±)-2-(4-chloro-2-methylphenoxy)-propanoic acid |
| mefenacet | 2-(2-benzothiazolyloxy-N-methyl-N-phenylacetamide |
| mefluidide | N-[2,4-dimethyl-5-[[(trifluoromethyl)sulfonyl]amino]phenyl]acetamide |
| methalpropalin | N-(2-methyl-2-propenyl)-2,6-dinitro-N-propyl-4-(trifluoromethyl)benzenamide |
| methabenzthiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl) amino]carbonyl]-amino]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 2-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aa,-4a,5a,7a,7aa-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitro-benzenesulfonamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridinecarboxylic acid |
| PPG-1013 | 5-[2-chloro-4-(trifluoromethyl)-phenoxy]-2-nitroacetophenone oxime-O-acetic acid, methyl ester |
| pretilachlor | α-chloro-2,6-diethyl-N-(2-propoxyethyl)acetanilide |
| procyazine | 2-[[4-chloro-6-(cyclopropylamino)-1,3,5-triazine-2-yl]amino]-2-methylpropanenitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| pyrazolate | 4-(2,4-dichlorobenzoyl)-1,3-dimethyl-pyrazol-5-yl-p-toluenesulphonate |
| pyrazon | 5-amino-4-chloro-2-phenyl-3(2H)-pyridazinone |
| pyrazosulfuron ethyl | ethyl S-[3-(4,6-dimethoxypyrimidin-2-yl)ureadosulfonyl]-1-methylpyrazole-4-carboxylate |
| quinclorac | 3,7-dichloro-8-quinoline carboxylic acid |
| quizalofop ethyl | (±)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| SK-233 | 1-(a,a-dimethylbenzyl)-3-(4-methylphenyl)urea |
| sulfometuron methyl | 2-[[[[(4,6-dimethyl-2-pyrimidinyl)-amino]carbonyl]amino]sulfonyl]-benzoic acid, methyl ester |

TABLE I-continued

| Common Name | Chemical Name |
|---|---|
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thiobencarb | S-[(4-chlorophenyl)methyl] diethylcarbamothioate |
| triallate | S-(2,3,3-trichloro-2-propenyl) bis(1-methylethyl)carbamothioate |
| triclopyr | [(3,5,6-trichloro-2-pyridinyl)oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

The herbicidal properties of the compounds of Formula I are evaluated as described below in the following tests.

As referred to in the tests below, Compound 1 means compounds of Formula I where R is (—CH$_2$C≡CH), X is Cl, Y is F, and Z is H. Compound 2 means compounds of Formula I where R and Z are taken together as

(—CH$_2$CHCH$_3$)

such that the linking oxygen is attached to the methine carbine, Y is F, and X is Cl. Compound 2 has the following structure:

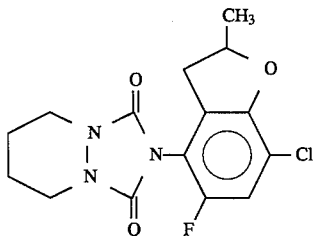

Compound 4 means compounds of Formula I where R and Z are taken together as

(—CH$_2$CHCH$_3$)

such that the linking oxygen is attached to the methine carbon, Y is Cl, and X is Cl. Compound 4 has the following structure:

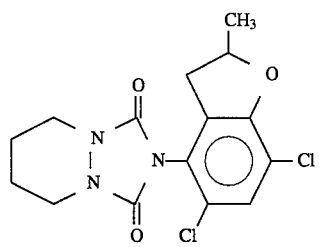

TEST A

Plastic tray liners with individual planting compartments are filled with planting medium and seeded separately with bermudagrass (*Cynodon dactylon*), broadleaf signalgrass (*Brachiaria platyphylla*), guineagrass (*Panicum maximum*), smooth crabgrass (*Digitaria ischaemum*), barnyardgrass (*Echinocloa crusgalli*), large crabgrass (*D. sanguinalis*), johnsongrass (*Sorghum halepense*), Texas panicum (*Panicum texanum*), sandbur (*Cenchrus echinatus*), itchgrass (*Rottboellia cochinchinensis*), goosegrass (*Eleusine indica*), dallisgrass (*Paspalum dilatatum*), annual bluegrass (*Poa annum*), alfalfa (*Medicago sativa*), Pueraria javanica, morningglory (Ipomea spp.) purslane (*Portulaca oleracea*), field bindweed (*Convolvulus arvensis*), ragweed (*Ambrosia elatior*), peanut (*Arachis hypogea*), purple nutsedge (*Cyperus rotundus*), yellow nutsedge (*C. esculeutus*), and Kentucky bluegrass sod (*Poa pratense*). Sugarcane node cuttings are planted in 15.2 cm plastic pots filled with planting medium.

The plantings are treated preemergence and postemergence with the compounds formulated in a non-phytotoxic spray solution. Plantings are staggered so that the preemergence and postemergence treatments are sprayed on the same day. Plants are visually rated 18 to 29 days after treatment (DAT) and compared with appropriate controls. The injury ratings are based on the scale of 0 to 100 where 0 indicates no effect, 20 indicates minimal effect and 100 indicates complete control. A dash (—) indicates not determined. The results are shown in Tables Aa–Ab.

TABLE Aa

| | Compound 1 | | | | | | |
|---|---|---|---|---|---|---|---|
| | 500 | 250 | 125 | 500 | 250 | 125 | |
| | Preemergence | | | Postemergence | | | g/ha |
| Sugarcane | — | — | — | 30 | 10 | 0 | |
| Bermudagrass | 100 | 100 | 100 | 100 | 90 | 30 | |
| Broadleaf signalgrass | 100 | 100 | 100 | 100 | 100 | 90 | |
| Guineagrass | 100 | 100 | 100 | 100 | 100 | 100 | |
| Smooth crabgrass | 100 | 100 | 100 | 100 | 0 | 0 | |
| Large crabgrass | 100 | 100 | 100 | 100 | 90 | 90 | |
| Johnson grass | 100 | 100 | 100 | 100 | 100 | 100 | |
| Texas panicum | 100 | 100 | 100 | 100 | 100 | 100 | |
| Sandbur | 90 | 100 | 90 | — | — | — | |
| Itchgrass | 100 | 100 | 100 | 100 | 60 | 50 | |
| Goosegrass | 100 | 100 | 100 | 100 | 100 | 100 | |
| Dallisgrass | 100 | 100 | 100 | 100 | 100 | 90 | |
| Annual bluegrass | 80 | 60 | 40 | 100 | 80 | 20 | |
| Kentucky bluegrass sod | — | — | — | 100 | 0 | 10 | |
| Alfalfa | 100 | 100 | 90 | 90 | 20 | 30 | |
| *Pueraria javanica* | 100 | 90 | 90 | — | — | — | |
| Morningglory | 100 | 100 | 100 | 100 | 100 | 100 | |
| Purslane | 100 | 100 | 100 | 100 | 100 | 100 | |
| Ragweed | 100 | 100 | 100 | 100 | 100 | 100 | |

TABLE Aa-continued

| | Compound 1 | | | | | | |
|---|---|---|---|---|---|---|---|
| | 500 | 250 | 125 | 500 | 250 | 125 | g/ha |
| | Preemergence | | | Postemergence | | | |
| Peanut | 70 | 70 | 60 | 80 | 30 | 60 | |
| Purple nutsedge | — | — | — | 80 | 50 | 20 | |
| Yellow nutsedge | — | — | — | 90 | 60 | 30 | |

TABLE Ab

| | Compound 2 | | |
|---|---|---|---|
| | 250 | 250 | |
| | Preemergence | Postemergence | g/ha |
| Bermudagrass | 100 | 0 | |
| Broadleaf signalgrass | 100 | 0 | |
| Guineagrass | 100 | 0 | |
| Smooth crabgrass | 100 | 0 | |
| Large crabgrass | 100 | 0 | |
| Johnsongrass | 90 | 0 | |
| Texas panicum | 100 | 0 | |
| Sandbur | 100 | 0 | |
| Itchgrass | 90 | 0 | |
| Goosegrass | 100 | — | |
| Annual bluegrass | 50 | 0 | |
| Kentucky bluegrass sod | — | 0 | |
| Alfalfa | 100 | 30 | |
| *Pueraria javanica* | 90 | — | |
| Morningglory | 100 | 60 | |
| Purslane | 100 | 100 | |
| Ragweed | 100 | 50 | |
| Peanut | 70 | 30 | |
| Purple nutsedge | 30 | 70 | |
| Yellow nutsedge | 60 | 60 | |

TEST B

Seeds of crabgrass (Digitaria spp.), barnyardgrass (*Echinochloa crus-galli*), giant foxtail (*Setaria faberi*), wild oats (*Avena fatua*), cheatgrass (*Bromus secalinus*), velvetleaf (*Abutilon theophrasti*), morningglory (Ipomoea spp.), cocklebur (*Xanthium pensylvanicum*), sorghum, corn, soybean, sugarbeet, cotton, rice, wheat, barley, cassia and purple nutsedge (*Cyperus rotundus*) tubers are planted and treated preemergence with the test chemicals dissolved in a non-phytotoxic solvent. At the same time, these crops and weed species are treated with a soil/foliage application. At the time of treatment, the plants ranged in height from 2 to 18 cm. Treated plants and controls are maintained in a greenhouse for sixteen days, after which all species are compared to controls and visually rated for response to treatment. The ratings, summarized in Tables Ba–Bc, are based on a numerical scale extending from 0=no injury, to 10=complete kill. The accompanying descriptive symbols have the following meanings:

C=chlorosis/necrosis
B=burn
D=defoliation
E=emergence inhibition
G=growth retardation
H=formative effect
U=unusual pigmentation
X=axillary stimulation
S=albinism
6Y=abscised buds or flowers

TABLE Ba

| | Compound 1 | | | | |
|---|---|---|---|---|---|
| | 400 | 100 | 400 | 100 | |
| | Preemergence | | Postemergence | | g/ha |
| Corn | 5C,9H | 5C,9H | 8B | 6B | |
| Soybean | 10C | 3C,9H | 10B | 10B | |
| Cotton | 10C | 10C | 10B | 10B | |
| Sorghum | 10C | 10C | 10B | 9B | |
| Morningglory | 10C | 10C | 10B | 10B | |
| Crabgrass | 10C | 8C | 10B | 9B | |
| Rice | 10C | 9C | 10B | 8B | |
| Barnyardgrass | 10C | 10C | 10B | 9B | |
| Spring wheat | 10C | 10C | 10B | 7B | |
| Sugar beet | 10C | 10C | 10B | 10B | |
| Wild oats | 10C | 10C | 10B | 8B | |
| Nutsedge | 10C | 10C | 9B | 7B | |
| Cocklebur | 10C | 9C | 10B | 10B | |
| Cassia | 10C | 10C | 10B | 10B | |

TABLE Bb

| | Compound 2 | | | | |
|---|---|---|---|---|---|
| | 400 | 50 | 400 | 50 | |
| | Preemergence | | Postemergence | | g/ha |
| Corn | 10H | 8H | 9B | 4B,7H | |
| Soybean | 10H | 10H | 10B | 10B | |
| Cotton | 10H | 8H | 10B | 10B | |
| Sorghum | 10H | 10H | 10B | 9B | |
| Velvetleaf | 10H | 10H | 10B | 10B | |
| Morningglory | 10H | 9H | 10B | 10B | |
| Giant foxtail | 10H | 9H | 10B | 9B | |
| Crabgrass | 10H | 9H | 10B | 9B | |
| Rice | 10H | 9H | 10B | 9B | |
| Barnyardgrass | 10H | 7H | 10B | 10B | |
| Spring wheat | 9H | 7H | 10B | 8B | |
| Winter barley | 10H | 2H | 9B | 2B | |
| Sugar beet | 10H | 10H | 10B | 9B | |
| Wild oats | 8H | 4H | 10B | 5B | |
| Nutsedge | 10H | 3H | 10B | 8B | |
| Cheatgrass | 6H | 6H | 4B,8H | 2B | |
| Cocklebur | 10H | 7H | 9B | 7B | |

TABLE Bc

| | Compound 4 | | | | |
|---|---|---|---|---|---|
| | 400 | 50 | 400 | 50 | |
| | Preemergence | | Postemergence | | g/ha |
| Corn | 7C | 0 | 6B | 3B | |
| Soybean | 2C,8G | 0 | 8B | 7B | |
| Cotton | 3C,7G | 0 | 10B | 10B | |
| Sorghum | 10C | 3C | 5B | 2B | |
| Velvetleaf | 10C | 10C | 10B | 8B | |
| Morningglory | 9C | 2G | 10B | 5B | |
| Giant foxtail | 10H | 9H | 9B | 5B | |
| Crabgrass | 10H | 3C,8H | 5B | 1B | |
| Rice | 8C | 2C | 7B | 3B | |
| Barnyardgrass | 9H | 0 | 9B | 3B | |
| Spring wheat | 3C,7H | 0 | 6B | 3B | |
| Winter barley | 1C | 0 | 4B | 2B | |
| Sugar beet | 9C | 7C | 7B | 6B | |
| Wild oats | 7C | 3G | 6B | 3B | |
| Nutsedge | 8C | 0 | 6B | 1B | |

TABLE Bc-continued

| | Compound 4 | | | | |
|---|---|---|---|---|---|
| | 400 | 50 | 400 | 50 | g/ha |
| | Preemergence | | Postemergence | | |
| Cheatgrass | | | | | |
| Cocklebur | 2C | 0 | 7B | 4B | |

TEST C

Postemergence

Three round pans (25 cm diameter by 12.5 cm deep) are filled with Sassafras sandy loam soil. One pan is planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*), and teaweed (*Sida spinosa*). The second pot is planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crus-galli*), corn (*Zea mays*), soybean (*Glycine max*), and giant foxtail (*Setaria faberi*). The third pot is planted with wheat (*Triticum aestivum*), barley (*Hordeum vulgare*), wild buckwheat (*Polygonum convolvulus*), downy brome (*Bromus tectorum*), sugarbeet (*Beta vulgaris*), wild oat (*Avena fatua*), common chickweed (*Stellaria media*), blackgrass (*Alopecurus myosuroides*), and rape (*Brassica napus*). The plants are grown for approximately fourteen days, then sprayed postemergence with the chemicals dissolved in a non-phytotoxic solvent.

Preemergence

Three round pans (25 cm diameter by 12.5 cm deep) are filled with Sassafras sandy loam soil. One pan is planted with nutsedge tubers, crabgrass, sicklepod, jimsonweed, velvetleaf, lambsquarters, rice, and teaweed. The second pot is planted with green foxtail, cocklebur, morningglory, cotton, johnsongrass, barnyardgrass, corn, soybean, and giant foxtail. The third pot is planted with wheat, barley, wild buckwheat, downy brome, sugarbeet, wild oat, common chickweed, blackgrass, and rape. The three pans are sprayed preemergence with the chemicals dissolved in a non-phytotoxic solvent.

Treated plants and controls are maintained in the greenhouse for approximately 24 days, then all rated plants are compared to controls and visually rated for plant response.

Response ratings used in Test B are used in some tests. In other tests the ratings are based on a scale of 0 to 100 where 0 indicates no effect, 20 minimal injury and 100 indicated complete control. A dash (—) response means no test is conducted. The results are shown in Table Ca–Cg.

TABLE Ca

| | Compound 1 | | | | |
|---|---|---|---|---|---|
| | 250 | 62 | 16 | 4 | g/ha |
| | Preemergence | | | | |
| Spring wheat | 10G | 10G | 2G | 0 | |
| Sugarbeet | 10G | 10G | 10G | 5G | |
| Wild oats | 10G | 9G | 0 | 0 | |

TABLE Ca-continued

| | Compound 1 | | | | |
|---|---|---|---|---|---|
| | 250 | 62 | 16 | 4 | g/ha |
| | Preemergence | | | | |
| Corn | 7G | 4G | 0 | 0 | |
| Soybean | 10G | 7G | 3G | 0 | |
| Cotton | 10G | 9G | 4G | 3G | |
| Velvetleaf | 10G | 10G | 10G | 5G | |
| Morningglory | 10G | 10G | 5G | 3G | |
| Crabgrass | 10G | 10G | 3G | 0 | |
| Barnyardgrass | 10G | 10G | 5G | 0 | |

TABLE Cb

| | Compound 1 | | | | |
|---|---|---|---|---|---|
| | 250 | 62 | 16 | 4 | g/ha |
| | Postemergence | | | | |
| Spring wheat | 9G | 4G | 0 | 0 | |
| Sugarbeet | 10G | 10G | 7G | 0 | |
| Wild oats | 10G | 8G | 0 | 0 | |
| Corn | 8G | 3G | 0 | 0 | |
| Soybean | 10G | 10G | 9G | 7G | |
| Cotton | 10G | 10G | 10G | 9G | |
| Velvetleaf | 10G | 10G | 10G | 3G | |
| Morningglory | 10G | 10G | 10G | 4G | |
| Crabgrass | 6G | 2G | 0 | 0 | |
| Giant foxtail | — | 6G | 0 | 0 | |
| Barnyardgrass | 10G | 4G | 0 | 0 | |

TABLE Cc

| | Compound 1 | | | | | | |
|---|---|---|---|---|---|---|---|
| | 250 | 62 | 16 | 250 | 62 | 16 | |
| | Preemergence | | | Postemergence | | | g/ha |
| Spring wheat | 90 | 20 | 0 | 100 | 60 | 0 | |
| Sugarbeet | 100 | 100 | 100 | 100 | 100 | 100 | |
| Rape | 100 | 100 | 100 | 100 | 100 | 100 | |
| Wild oats | 100 | 90 | 30 | 100 | 100 | 20 | |
| Blackgrass | 100 | 100 | 40 | 100 | 80 | 30 | |
| Corn | 100 | 70 | 40 | 100 | 70 | 30 | |
| Soybean | 100 | 100 | 40 | 100 | 100 | 60 | |
| Cotton | 100 | 100 | 60 | 100 | 100 | 100 | |
| Velvetleaf | 100 | 100 | 100 | 100 | 100 | 100 | |
| Morningglory | 100 | 100 | 90 | 100 | 100 | 100 | |
| Crabggrass | 100 | 100 | 90 | 100 | 70 | 40 | |
| Giant foxtail | 100 | 100 | — | 100 | 100 | 50 | |
| Barnyardgrass | 100 | 100 | 70 | 100 | 100 | 50 | |
| Johnson grass | 100 | 100 | 100 | 100 | 100 | 60 | |
| Nutsedge | 100 | 60 | 20 | 100 | 70 | 30 | |
| Cocklebur | 100 | 100 | 100 | 100 | 100 | 70 | |
| Teaweed | 100 | 100 | 100 | 100 | 100 | 100 | |
| Cassia | 100 | 100 | 100 | 100 | 100 | 100 | |
| Johnsonweed | 100 | 100 | 100 | 100 | 100 | 100 | |
| Rice | 100 | 100 | 100 | 100 | 100 | 100 | |

TABLE Cd

| | Compound 2 | | | | |
|---|---|---|---|---|---|
| | 250 | 62 | 16 | 4 | g/ha |
| | Preemergence | | | | |
| Spring wheat | 100 | 50 | 0 | 0 | |
| Winter barley | 70 | 40 | 0 | 0 | |
| Sugarbeet | 100 | 100 | 100 | 70 | |
| Rape | 100 | 100 | 90 | 70 | |
| Wild oats | 100 | 100 | 50 | 30 | |
| Blackgrass | 80 | 50 | 0 | 0 | |
| Downy brome | 30 | 0 | 0 | 0 | |

TABLE Cd-continued

| | Compound 2 | | | | |
|---|---|---|---|---|---|
| | 250 | 62 | 16 | 4 | |
| | Preemergence | | | | g/ha |
| Lambsquarters | 100 | 100 | 100 | 100 | |
| Wild buckwheat | 100 | 100 | 100 | 90 | |
| Chickweed | 60 | 30 | 0 | 0 | |
| Corn | 90 | 60 | 30 | 0 | |
| Soybean | 100 | 90 | 70 | 0 | |
| Cotton | 100 | 80 | 40 | 30 | |
| Velvetleaf | 100 | 100 | 100 | 70 | |
| Morningglory | 100 | 100 | 80 | 30 | |
| Crabgrass | 100 | 100 | 90 | 60 | |
| Giant foxtail | 100 | 100 | 100 | 30 | |
| Barnyardgrass | 100 | 90 | 60 | 30 | |
| Johnson grass | 100 | 100 | 80 | 30 | |
| Nutsedge | 100 | 100 | 50 | 30 | |
| Green foxtail | 100 | 100 | 100 | 30 | |
| Cocklebur | 90 | 80 | 60 | 20 | |
| Teaweed | 100 | 100 | 100 | 90 | |
| Cassia | 100 | 100 | 100 | 30 | |
| Jimsonweed | 100 | 100 | 100 | 60 | |
| Rice | 100 | 90 | 70 | 30 | |

TABLE Ce

| | Compound 2 | | | | |
|---|---|---|---|---|---|
| | 250 | 62 | 16 | 4 | |
| | Postemergence | | | | g/ha |
| Spring wheat | 100 | 70 | 20 | 0 | |
| Winter barley | 80 | 30 | 0 | 0 | |
| Sugarbeet | 100 | 100 | 90 | 40 | |
| Rape | 100 | 100 | 100 | 90 | |
| Wild oats | 100 | 80 | 30 | 0 | |
| Blackgrass | 100 | 70 | 20 | 0 | |
| Downy brome | 90 | 30 | 0 | 0 | |
| Lambsquarters | 100 | 100 | 100 | 100 | |
| Wild buckwheat | 100 | 100 | 100 | 100 | |
| Chickweed | 100 | 100 | 40 | 10 | |
| Corn | 30 | 10 | 0 | 0 | |
| Soybean | 100 | 100 | 90 | 60 | |
| Cotton | 100 | 100 | 100 | 100 | |
| Velvetleaf | 100 | 100 | 100 | 80 | |
| Morningglory | 100 | 100 | 50 | — | |
| Crabgrass | 100 | 50 | 30 | 20 | |
| Giant foxtail | 100 | 100 | 20 | 0 | |
| Barnyardgrass | 100 | 100 | 50 | 10 | |
| Johnson grass | 100 | 100 | 40 | 20 | |
| Nutsedge | 100 | 90 | 40 | — | |
| Green foxtail | 100 | 100 | 30 | 20 | |
| Cocklebur | 100 | 40 | 40 | 30 | |
| Teaweed | 100 | 100 | 100 | 50 | |
| Cassia | 90 | 50 | 50 | 20 | |
| Jimsonweed | 100 | 100 | 100 | 80 | |
| Rice | 100 | 100 | 70 | 30 | |

TABLE Cf

| | Compound 4 | | | | |
|---|---|---|---|---|---|
| | 500 | 250 | 62 | 16 | |
| | Preemergence | | | | g/ha |
| Spring wheat | 30 | 20 | 10 | 0 | |
| Winter barley | 30 | 20 | 20 | 10 | |
| Sugarbeet | 100 | 100 | 90 | 80 | |
| Rape | 100 | 100 | 40 | 30 | |
| Wild oats | 30 | 20 | 0 | 0 | |
| Blackgrass | 90 | 90 | 40 | 20 | |
| Downy brome | 20 | 0 | 0 | 0 | |
| Lambsquarters | 100 | 100 | 100 | 50 | |
| Wild buckwheat | 100 | 100 | 100 | 50 | |
| Chickweed | 0 | 0 | 0 | 0 | |
| Corn | 90 | 90 | 50 | 40 | |
| Soybean | 60 | 40 | 20 | 0 | |
| Cotton | 70 | 50 | 20 | 0 | |
| Velvetleaf | 100 | 100 | 90 | 30 | |
| Morningglory | 90 | 90 | 50 | 30 | |
| Crabgrass | 100 | 90 | 85 | 50 | |
| Giant foxtail | 100 | 100 | 90 | 30 | |
| Barnyardgrass | 100 | 100 | 90 | 30 | |
| Johnson grass | 100 | 100 | 40 | 20 | |
| Nutsedge | 60 | 20 | 0 | — | |
| Green foxtail | 100 | 100 | 90 | 50 | |
| Cocklebur | 50 | 30 | 0 | 0 | |
| Teaweed | 100 | 100 | 100 | 30 | |
| Cassia | 70 | 40 | 20 | 20 | |
| Jimsonweed | 100 | 100 | 50 | 30 | |
| Rice | 100 | 90 | 70 | 30 | |

TABLE Cg

| | Compound 4 | | | |
|---|---|---|---|---|
| | 500 | 250 | 62 | |
| | Postemergence | | | g/ha |
| Spring wheat | 10 | 0 | 0 | |
| Winter barley | 0 | 0 | 0 | |
| Sugarbeet | 100 | 60 | 10 | |
| Rape | 100 | 90 | 50 | |
| Wild oats | 20 | 0 | 0 | |
| Blackgrass | 50 | 0 | 0 | |
| Downy brome | 0 | 0 | 0 | |
| Lambsquarters | 100 | 100 | 80 | |
| Wild buckwheat | 100 | 100 | 100 | |
| Chickweed | — | 70 | — | |
| Corn | 10 | 0 | 0 | |
| Soybean | 80 | 80 | 70 | |
| Cotton | 80 | 60 | 50 | |
| Velvetleaf | 100 | 100 | 100 | |
| Morningglory | 60 | 30 | 30 | |
| Crabgrass | 70 | 60 | 30 | |
| Giant foxtail | — | 70 | 30 | |
| Barnyardgrass | 90 | 40 | 0 | |
| Johnson grass | 100 | 30 | 10 | |
| Nutsedge | 70 | 40 | 10 | |
| Green foxtail | 100 | 80 | 20 | |
| Cocklebur | 60 | 30 | 20 | |
| Teaweed | 100 | 100 | 90 | |
| Cassia | 50 | 50 | 30 | |
| Jimsonweed | 100 | 90 | 80 | |
| Rice | 20 | 20 | 10 | |

TEST D

Seeds of spring wheat (*Triticum aestivum*), winter wheat (*T. aestivum*), spring barley (*Hordeum vulgare*), winter barley (*H. vulgare*), sugarbeet (*Beta vulgaris*), rape (*Brassica napus*), wild oat (*Avena fatua*), downy brome (*Bromus tectorium*), cheatgrass (*B. secalinus*), blackgrass (*Alopercurus myosuroides*), annual bluegrass (*Poa annum*), green foxtail (*Setaria viridis*), Italian ryegrass (*Lolium multiflorum*), jointed goatgrass (*Aegilops cylindrica*), *Matricaria indora*, Galium spp., Russian thistle (*Salsola kali*), lambsquarters (*Chenopodium album*), kochia (*Kochia scoparia*), black nightshade (*Solanum nigrum*), speedwell (*Veronica persica*), wild buckwheat (*Polygonium convolvulus*), viola (*Viola* spp.), *Veronica hederaefolia* and field pennycress (*Thlapsi arvensis*) are placed in 26 cm plastic pans containing pasteurized sandy loam soil. Plantings are maintained in the greenhouse for 28 days at which time the postemergence treatments are applied using compounds formulated in a non-phytotoxic solvent. The preemergence portion of the test is seeded just before spraying. The postemergence treatments also contained wild oats and blackgrass at 1-leaf and 3-leaf growth stages. All treatments are held in the greenhouse for an additional 21 days at which time visual assessments of plant injury are made using a scale of 0 to 100 where 0 indicates no effect, 20 indicates minimal injury and 100 indicates complete control. The results are shown in Tables Da and Db.

TABLE Da

| | Compound 1 | | | | |
|---|---|---|---|---|---|
| | 64 | 32 | 16 | 8 | |
| | | Preemergence | | | g/ha |
| Spring wheat | 100 | 80 | 50 | 20 | |
| Winter wheat | 90 | 80 | 50 | 10 | |
| Spring barley | 70 | 40 | 20 | 10 | |
| Winter barley | 70 | 50 | 20 | 20 | |
| Sugarbeet | 100 | 100 | 100 | 100 | |
| Rape | 100 | 100 | 100 | 70 | |
| Wild oats | 80 | 70 | 60 | 40 | |
| Downy brome | 90 | 70 | 40 | 20 | |
| Cheatgrass | 70 | 70 | 50 | 10 | |
| Blackgrass | 70 | 70 | 60 | 20 | |
| Annual bluegrass | 40 | 40 | 30 | 10 | |
| Green foxtail | 100 | 100 | 100 | 80 | |
| Italian ryegrass | 90 | 90 | 70 | 40 | |
| Goatgrass | 30 | 30 | 20 | 0 | |
| *Matricaria indora* | 100 | 100 | 100 | 100 | |
| Galium | 30 | 0 | 0 | 0 | |
| Russian thistle | 100 | 100 | 100 | 100 | |
| Lambsquarters | 100 | 100 | 100 | 100 | |
| Kochia | 100 | 100 | 100 | 70 | |
| Black nightshade | 100 | 100 | 100 | 100 | |
| Speedwell | 100 | 100 | 100 | 100 | |
| *Veronica hederaefolia* | 100 | 100 | 70 | 60 | |
| Wild buckwheat | 100 | 100 | 100 | 100 | |
| Viola | 80 | 70 | 50 | 20 | |
| Field pennycress | 100 | 100 | 100 | 100 | |

TABLE Db

| | Compound 1 | | | | |
|---|---|---|---|---|---|
| | 64 | 32 | 16 | 8 | |
| | | Postemergence | | | g/ha |
| Spring wheat | 50 | 50 | 30 | 20 | |
| Winter wheat | 50 | 30 | 30 | 10 | |
| Spring barley | 100 | 30 | 20 | 20 | |
| Winter barley | 40 | 40 | 30 | 20 | |
| Sugarbeet | 100 | 90 | 90 | 80 | |
| Rape | 100 | 100 | 80 | 60 | |
| Wild oats | | | | | |
| 1-leaf | 100 | 60 | 30 | 20 | |
| 3-leaf | 60 | 50 | 30 | 10 | |
| Downy brome | 40 | 10 | 10 | 10 | |
| Cheatgrass | 60 | 30 | 20 | 0 | |
| Blackgrass | | | | | |
| 1-leaf | 70 | 20 | 20 | 10 | |
| 3-leaf | 30 | 20 | 20 | 10 | |
| Annual bluegrass | 20 | 20 | 10 | 10 | |
| Green foxtail | 100 | 100 | 70 | 60 | |
| Italian ryegrass | 90 | 60 | 20 | 10 | |
| Goatgrass | 30 | 20 | 20 | 10 | |
| *Matricaria indora* | 100 | 100 | 60 | 30 | |
| Galium | 70 | 40 | 40 | 20 | |
| Russian thistle | 100 | 100 | 100 | 100 | |
| Lambsquarters | 100 | 60 | 60 | 50 | |
| Kochia | 100 | 100 | 70 | 60 | |
| Black nightshade | 100 | 100 | 100 | 80 | |

TABLE Db-continued

| | Compound 1 | | | | |
|---|---|---|---|---|---|
| | 64 | 32 | 16 | 8 | |
| | | Postemergence | | | g/ha |
| Speedwell | 100 | 80 | 80 | 60 | |
| *Veronica hederaefolia* | 100 | 100 | 100 | 100 | |
| Wild buckwheat | 100 | 100 | 100 | 100 | |
| Viola | 60 | 40 | 40 | 0 | |
| Field pennycress | 100 | 100 | 50 | 40 | |

TEST E

Seeds of downy brome (*Bromus tectorum*), kochia (*Kochia scoparia*), optionally Russian thistle (*Salsola kali*), wild oats (*Avena fatua*), field bindweed (*convolvulus arvensis*), rye (*Secale cereale*), green foxtail (*Setaria viridis*) and winter wheat (*Triticum aestivum*) are placed in 26-cm plastic pans containing a pasteurized sandy loam soil (pH 6.5, 1% organic matter). Plantings are maintained in the greenhouse for 28 days at which time the postemergence treatments are applied using a nonphytotoxic solvent as the carrier for the herbicide. The preemergence segment of the test is seeded immediately before herbicide application using seeds of downy brome (*Bromus tectorum*), kochia (*Kochia scoparia*), optionally Russian thistle (*Salsola kali*), wild oats (*Avena factua*), field bindweed (*Convolvulus arvensis*), rye (*Secale cereale*), green foxtail (*Setaria viridis*), jointed goatgrass (*Aegilops cyclindrica*), wild buckwheat (*Polygonium convolvus*), pigweed (*Amaranthus retroflexus*) and lambsquarters (*Chenopodium album*). A separate pot is prepared using a sandy loam soil which contained the crop species barley (*Hordeum vulgare*), winter wheat (*Triticum aestivum*), spring wheat (*Triticum aestivum*), sorghum (*Sorghum bicolor*) and corn (*Zea mays*).

All treatments are maintained in the greenhouse for an additional 21 days at which time visual assessments of weed control are made using a scale of 0 to 100 for each species where 0 represents no control and 100 represents complete control. The results are shown in Tables Ea–Ec.

TABLE Ea

| | Compound 1 | | | | | |
|---|---|---|---|---|---|---|
| | 1000 | 250 | 125 | 64 | 32 | g/ha |
| Postemergence | | | | | | |
| Russian thistle | 100 | 100 | 100 | 100 | 100 | |
| Kochia | 100 | 100 | 100 | 100 | 100 | |
| Downy Brome | 90 | 90 | 90 | 80 | 30 | |
| Green foxtail | 100 | 100 | 100 | 100 | 100 | |
| Wild oat | 100 | 100 | 100 | 90 | 90 | |
| Wheat | 100 | 90 | 90 | 80 | 50 | |
| Rye | 90 | 80 | 70 | 70 | 20 | |
| Field bindweed | 100 | 100 | 100 | 100 | 100 | |
| Preemergence | | | | | | |
| Wheat | 100 | 100 | 90 | 90 | 20 | |
| Barley | 100 | 90 | 80 | 60 | 20 | |
| Corn | 100 | 90 | 90 | 90 | 0 | |
| Sorghum | 100 | 100 | 100 | 100 | 0 | |

TABLE Eb

| | \multicolumn{6}{c}{Compound 1} |
|---|---|---|---|---|---|---|
| | 1000 | 250 | 125 | 64 | 32 | g/ha |
| Postemergence | | | | | | |
| Russian thistle | 100 | 100 | 100 | 100 | 100 | |
| Kochia | 100 | 100 | 100 | 100 | 100 | |
| Downy Brome | 100 | 90 | 80 | 70 | 30 | |
| Green foxtail | 100 | 100 | 100 | 100 | 100 | |
| Wild oat | 100 | 100 | 100 | 100 | 80 | |
| Wheat | 100 | 90 | 90 | 90 | 60 | |
| Rye | 100 | 100 | 100 | 100 | 90 | |
| Field bindweed | 100 | 100 | 100 | 100 | 100 | |
| Preemergence | | | | | | |
| Wheat | 100 | 90 | 80 | 80 | 70 | |
| Barley | 100 | 80 | 80 | 70 | 40 | |
| Corn | 80 | 80 | 70 | 50 | 50 | |
| Sorghum | 100 | 100 | 90 | 80 | 70 | |

TABLE Ec

| | \multicolumn{5}{c}{Compound 1} |
|---|---|---|---|---|---|
| | 250 | 125 | 64 | 32 | g/ha |
| Postemergence | | | | | |
| Russian thistle | 100 | 100 | 95 | 95 | |
| Kochia | 100 | 100 | 100 | 100 | |
| Downy Brome | 95 | 70 | 50 | 30 | |
| Green foxtail | 100 | 100 | 100 | 75 | |
| Wild oat | 100 | 95 | 70 | 50 | |
| Wheat | 100 | 80 | 50 | 45 | |
| Rye | 60 | 50 | 40 | 40 | |
| Field bindweed | 100 | 100 | 100 | 100 | |
| Preemergence | | | | | |
| Wheat | 100 | 100 | 70 | 30 | |
| Barley | 100 | 70 | 40 | 20 | |
| Corn | 98 | 90 | 80 | 70 | |
| Sorghum | 100 | 100 | 80 | 70 | |
| Winter wheat | 90 | 90 | 70 | 40 | |
| Russian thistle | 100 | 100 | 100 | 95 | |
| Kochia | 100 | 100 | 100 | 100 | |
| Downy brome | 98 | 75 | 60 | 30 | |
| Green foxtail | 100 | 100 | 100 | 100 | |
| Wild oats | 100 | 95 | 75 | 70 | |
| Rye | 40 | 40 | 40 | 30 | |
| Field bindweed | 100 | 100 | 100 | 100 | |
| Jointed goatgrass | 75 | 40 | 45 | 30 | |
| Wild buckwheat | 100 | 100 | 100 | 100 | |
| Lambsquarters | 100 | 100 | 100 | 100 | |
| Pigweed | 100 | 100 | 100 | 95 | |

TEST F

The Corn and Sorghum Herbicide Test included the following species in both the preemergence and postemergence evaluations:

| | SPECIES | |
|---|---|---|
| Category | Common Name | Scientific Name |
| Crops | Corn | *Zea mays* |
| | Soybean | *Glycine max* |
| | Sorghum | *Sorghum bicolor* |
| Grasses | Green foxtail | *Setaria viridis* |
| | Giant foxtail | *Setaria faberii* |
| | Johnsongrass | *Sorghum halepense* |
| | Barnyardgrass | *Echinochloa crus-galli* |
| | Fall panicum | *Panicum dichotomiflorum* |
| | Crabgrass | *Digitaria sanguinalis* |
| | Nutsedge | *Cyperus rotundus* |
| Broadleaves | Cocklebur | *Xanthium pensylvanicum* |
| | Morningglory | *Ipomoea hederacea* |
| | Velvetleaf | *Abutilon theophrasti* |
| | Jimsonweed | *Datura stramonium* |
| | Lambsquarters | *Chenopodium album* |
| | Pigweed | *Amaranthus retroflexus* |
| | Smartweed | *Polygonum persicaris* |

Postemergence

Postemergence plantings are grown in Sassafras sandy loam soil. Corn and soybeans are grown in separate 25 cm diameter containers. Sorghum and the seven grass weed species are grown in two 18 cm diameter containers, 4 species per container. The seven broadleaf weed species are also grown in two 18 cm diameter containers, 4 species in one container, 3 species in the second container. One additional planting of corn in an 18 cm diameter container is made. The soil surface of this additional container of corn is covered with the absorbent, perlite, before spray treatment so that test chemicals would enter the plant only via the foliage. The plants are grown 10–21 days, dependent upon the species and then sprayed postemergence with the test chemicals dissolved in a non-phytotoxic solvent.

Preemergence

Preemergence plantings are grown in fertilized Tama silt loam soil. These plantings are identical to those described in the postemergence section, with the exception of the corn planting having perlite covering the soil surface. These plantings are made the day of or the day before spraying the test chemicals dissolved in a non-phytotoxic solvent.

Treated plants and controls are maintained in the greenhouse for 2 to 4 weeks. Visual ratings are made using a scale of 0 to 100 where 0 indicates no effect, and 100 indicates complete control. The results are shown in Table F.

TABLE F

| | \multicolumn{6}{c}{Compound 1} | |
|---|---|---|---|---|---|---|---|
| | 250 | 125 | 64 | 32 | 16 | 8 | |
| | \multicolumn{6}{c}{Postemergence} | g/ha |
| Corn | 95 | 85 | 55 | 45 | 35 | 0 | |
| Sorghum | 100 | 100 | 100 | 85 | 75 | 40 | |
| Soybean | 100 | 100 | 100 | 90 | 75 | 50 | |
| Green foxtail | 100 | 100 | 95 | 80 | 65 | 35 | |
| Giant foxtail | 100 | 100 | 95 | 80 | 60 | 30 | |
| Fall panicum | 100 | 100 | 100 | 95 | 65 | 20 | |
| Crabgrass | 95 | 85 | 60 | 35 | 0 | 0 | |
| Barnyardgrass | 100 | 85 | 65 | 35 | 20 | 0 | |
| Johnson grass | 100 | 100 | 95 | 85 | 60 | 0 | |
| Nutsedge | 100 | 95 | 85 | 65 | 35 | 0 | |
| Velvetleaf | 100 | 100 | 100 | 100 | 100 | 100 | |
| Cocklebur | 100 | 100 | 100 | 100 | 60 | 20 | |
| Smartweed | 100 | 100 | 100 | 95 | 60 | 40 | |
| Lambsquarters | 100 | 100 | 95 | 90 | 80 | 50 | |
| Pigweed | 100 | 100 | 85 | 75 | 40 | 30 | |
| Ivyleaf | | | | | | | |
| Morningglory | 100 | 100 | 100 | 100 | 100 | 65 | |
| Jimsonweed | 100 | 100 | 100 | 100 | 95 | 45 | |

TEST G

Stem cuttings of Mikania spp, lantana (*Lantana camara*) and *Nephrolepis cordata* are planted in separate 15.2 cm plastic pots filled with greenhouse planting medium. The plants are grown in the greenhouse until used.

The vigorously growing plants are sprayed postemergence with Compound 1 in a nonphytotoxic solvent. The treated plants are visually rated 45 DAT and compared with appropriate controls. The injury ratings are based on the scale of 0 to 100 where 0 indicates no effect, 20 indicates minimal effect and 100 indicates complete control. The results are shown in Table G.

TABLE G

|  | Rate g/ha | Lantana | Mikania spp. | N. cordata |
|---|---|---|---|---|
| Compound 1 | 1000 | 50 | 75 | 60 |
|  | 500 | 0 | 55 | 40 |
|  | 250 | 0 | 30 | 20 |

TEST H

Large fiberglass tubs are filled with planting medium and planted with Rough lemon (Citrus sp.) rooted cutting, apple (Malus sp.) seedlings, grape (Vitis sp.) seedlings and pineapple (*Ananas comosus*) suckers are planted in one tube. A second tub is seeded with swollen fingergrass (*Chloris inflata*), guineagrass (*Panicum maximum*), goosegrass (*Eleusine indica*), itchgrass (*Rottboellia cochinchinensis*), Johnson grass (*Sorghum halapense*), large crabgrass (*Digitaria sanguinalis*), black nightshade (*Solanum nigrum*), pigweed (Amaranthus spp.), lambsquarters (Chenopodium spp), morningglory (Ipomoea sp.), common ragweed (*Ambrosia elatior*) and spanish needles (*Bidens pilosa*) seeds. The rough lemon, apple and grape plants are sprayed to simulate field type treatments where the spray covers only the trunk of the plant, the pineapple is sprayed postemergence and the weeds are treated preemergence. The tubs are treated with Compound 1 formulated in a non-phytotoxic solvent. Plants are visually rated 33 DAT and compared with appropriate controls. The injury rating scale used in Test G is also used. The results are shown in Table H.

TABLE H

|  | Compound 1 | | | | |
|---|---|---|---|---|---|
|  | 500 | 250 | 125 | 64 | g/ha |
| Postemergence | | | | | |
| Pineapple | 80 | 60 | 30 | 0 | |
| Preemergence | | | | | |
| Rough lemon | 0 | 0 | 0 | 0 | |
| Apple | 25 | 15 | 20 | 0 | |
| Grapes | 100 | 100 | 65 | 100 | |
| Swollen fingergrass | 100 | 100 | 100 | 100 | |
| Guineagrass | 100 | 100 | 100 | 100 | |
| Goosegrass | 100 | 100 | 100 | 100 | |
| Itchgrass | 100 | 100 | 90 | 50 | |
| Johnson grass | 100 | 100 | 100 | 90 | |
| Large crabgrass | 100 | 100 | 100 | 100 | |
| Black nightshade | 100 | 100 | 100 | 100 | |
| Pigweed | 100 | 100 | 100 | 100 | |
| Lambsquarters | 100 | 100 | 100 | 100 | |
| Morningglory | 100 | 100 | 100 | 80 | |
| Ragweed | 100 | 100 | 100 | 100 | |

TABLE H-continued

|  | Compound 1 | | | | |
|---|---|---|---|---|---|
|  | 500 | 250 | 125 | 64 | g/ha |
| Spanish needles | 100 | 80 | 20 | 0 | |

TEST I

Loblolly pine (*Pinus taeda*), swamp chestnut oak (*Ouercus michauxii*) and red cedar are planted in a 30-liter plastic pot. Rooted raspberry (Rubrus spp.) cuttings are also planted in another 30-liter plastic pot filled with planting medium. The plants are grown in the greenhouse for over three months before being sprayed.

Plants are sprayed postemergence with Compound 1 formulated in a non-phytotoxic solvent. The treated plants are visually rated 31 DAT and compared with appropriate controls. Plant injury scale used in Test G is used in this test also. The results are shown in Table I.

TABLE I

|  |  | Plant Injury Rating | | | |
|---|---|---|---|---|---|
|  | Rate g/ha | Loblolly pine | Swamp Chestnut Oak | Red Cedar | Raspberry |
| Compound 1 | 1000 | 0 | 80 | 0 | 30 |
|  | 500 | 0 | 80 | 0 | 20 |
|  | 250 | 0 | 80 | 0 | 10 |
|  | 125 | 0 | 80 | 0 | 0 |
|  | 64 | 0 | 80 | 0 | 0 |

TEST J

Rooted cuttings of rough lemon (Citrus sp.) are planted in 30-liter plastic pots. These pots are also seeded with guineagrass (*Panicum maximum*), pigweed (Amaranthus spp.), narrowleaf panicum (*P. maximum*), Texas panicum (*P. texanum*) seeds and yellow nutsedge tubers. Two 20.3 cm pots are filled with planting medium. One is planted with apple (Malus spp.) seedling and seeded with Johnsongrass (*Sorghum halapense*), blackgrass (*Alopecurus myosuroides*) seeds and *Paspalum conjugatum* node cuttings. The second pot is planted with grape (Vitis spp.) seedlings and seeded with wild radish (*Raphanus raphanistrum*).

The citrus and grapes are sprayed to simulate field type post-directed herbicide application while the grapes and weeds are treated postemergence with Compound 1 formulated in a non-phytotoxic spray solvent. Plants are visually rated 36 DAT and compared with the appropriate controls. The injury rating scale used in Table G is also used. The results are shown in Table J.

TABLE J

|  | Compound 1 | | | | | |
|---|---|---|---|---|---|---|
|  | 1000 | 500 | 250 | 125 | 64 | g/ha |
| Post-directed | | | | | | |
| Rough lemon | 0 | 0 | 0 | 0 | 0 | |
| Apple | 0 | 0 | 0 | 0 | 0 | |
| Postemergence | | | | | | |
| Grapes | 0* | 0* | 0* | 0* | — | |
| Guineagrass | 100 | 80 | 70 | 70 | 0 | |

TABLE J-continued

|  | Compound 1 | | | | | |
| --- | --- | --- | --- | --- | --- | --- |
|  | 1000 | 500 | 250 | 125 | 64 | g/ha |
| Yellow nutsedge | 100 | 80 | 60 | 0 | 0 | |
| Pigweed | 90 | 90 | 80 | 0 | 0 | |
| Narrowleaf panicum | 90 | 70 | 60 | 0 | 0 | |
| Texas panicum | 100 | 100 | 100 | 60 | 60 | |
| *Paspalum conjugatum* | 40 | 20 | 0 | 0 | 0 | |
| Johnson grass | 70 | 70 | 70 | 30 | 0 | |
| Wild radish | 90 | 50 | 30 | 30 | — | |
| Blackgrass | 90 | 20 | 0 | 0 | — | |

*initial burn but plant recovered.

TEST K

Coffee (Coffea spp.), Mikania spp. cuttings and thistle rhizomes are planted in separate 15.2 cm pots filled with planting medium. 19-liter pots filled with planting medium are planted with Eucalyptus spp. The plants are grown in the greenhouse until used.

Plants are treated postemergence with Compound 1, formulated in a non-phytotoxic solvent. One coffee plant is treated post-directed to simulate field treatment. Plants are visually rated 29 DAT and compared with the appropriate controls. Plant injury rating scale used in Test G is used in this test also. The results are shown in Table K.

TABLE K

|  | Compound 1 | | | | |
| --- | --- | --- | --- | --- | --- |
|  | 1000 | 500 | 250 | 125 | g/ha |
| Post-directed | | | | | |
| Coffee | 10 | 10 | 5 | — | |
| Postemergence | | | | | |
| Coffee | 40* | 40* | 40* | — | |
| Eucalyptus | 70 | 60 | 50 | — | |
| Mikania | 90 | 80 | 70 | 60 | |
| Thistle | 20 | 20 | 20 | 10 | |

*initial burn

TEST L

Banana (Musa sp.) plants growing in 20.3 cm pots were used in this test. Plants at the 11-leaf stage were sprayed with Compound 1 in a non-phytotoxic solvent. The treatments were applied over-the-top in one group of plants and post-directed to simulate field-type treatment in another group. Treated plants were visually rated 54 DAT and compared with the appropriate controls. Plant injury rating scale used in Test G is used in this test also. The results are shown in Table L.

TABLE L

| | Compound 1 250 g/ha | |
| --- | --- | --- |
|  | Over-the-Top | Post-directed |
| Banana | 0 | 0 |

TEST M

In a field trial, plots with first year citrus (gragefruit and orange) trees were used. The plots also had the weeds crabgrass (Digitaria spp.), Florida pusley (*Richardia scabra*), and prostrate spurge (*Euphorbia supina*) at the mature and blooming stage of growth. Plots were sprayed with Compound 1 in a non-phytotoxic solvent. Treatments were applied post-directed to the citrus and postemergence to the weeds. Plants were visually rated 112 DAT and compared with the controls using the 0 to 100 injury rating scale, where 0=no effect and 100=complete control. The results are shown in Table M.

TABLE M

|  | Compound 1 | | | |
| --- | --- | --- | --- | --- |
|  | 64 | 32 | 16 | ounces/acre |
| Citrus | 0 | 0 | 0 | |
| Crabgrass | 98 | 98 | 85 | |
| Florida pusley | 100 | 97 | 85 | |
| Prostrate spurge | 100 | 100 | 97 | |

What is claimed is:

1. A method for controlling undesired weeds in crops selected from the group of citrus, sugarcane, coffee, oil palm, grapes, and nut trees which comprises applying to the locus of the weeds a herbicidally effective amount of a compound of Formula I

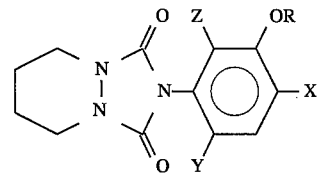

wherein
R is propargyl;
X is Cl;
Y is F; and
Z is H.

2. The method of claim 1 wherein the crop is citrus.
3. The method of claim 1 wherein the crop is sugarcane.
4. The method of claim 1 wherein the crop is coffee.
5. The method of claim 1 wherein the crop is oil palm.
6. The method of claim 1 wherein the crop is grapes.

* * * * *

UNITED STATES PATENT AND TRADEMARK OFFICE
CERTIFICATE OF CORRECTION

PATENT NO. : 5,480,856

DATED : January 2, 1996

INVENTOR(S) : Kofi Sam Amuti

It is certified that error appears in the above-identified patent and that said Letters Patent is hereby corrected as shown below:

Column 1, line 52, delete "-CH(CH$_3$)C=CH" and insert -- -CH(CH$_3$)C≡CH --.

Column 2, line 57, delete "-(CH$_3$)C≡CH" and insert -- -CH(CH$_3$)C≡CH --.

Column 4, line 55, insert --Wettable Powder-- between "Example A" and the top line of the list of ingredients.

Column 5, line 2, insert --Wettable Powder-- between "Example B" and the top line of the list of ingredients.

Column 5, line 20, insert --Granule-- between "Example C" and the top line of the list of ingredients.

Column 5, line 33, insert --Extruded Pellet-- between "Example D" and the top line of the list of ingredients.

Column 5, line 55, insert --Low Strength Granule-- between "Example E" and the top line of the list of ingredients.

Column 6, line 2, insert --Granule-- between "Example F" and the top line of the list of ingredients.

Column 6, line 27, insert --Aqueous Suspension-- between "Example G" and the top line of the list of ingredients.

Column 6, line 45, insert --High Strength Concentrate-- between "Example H" and the top line of the list of ingredients.

UNITED STATES PATENT AND TRADEMARK OFFICE
CERTIFICATE OF CORRECTION

PATENT NO. : 5,480,856

DATED : January 2, 1996

INVENTOR(S) : Kofi Sam Amuti

It is certified that error appears in the above-identified patent and that said Letters Patent is hereby corrected as shown below:

Column 6, line 60, insert --Wettable Powder-- between "Example I" and the top line of the list of ingredients.

Column 7, line 8, insert --Wettable Powder-- between "Example J" and the top line of the list of ingredients.

Column 7, line 24, insert --Oil Suspension-- between "Example K" and the top line of the list of ingredients.

Column 7, line 40, insert --Dust-- between "Example L" and the top line of the list of ingredients.

Column 7, line 55, insert --Oil Suspension-- between "Example M" and the top line of the list of ingredients.

Column 13, line 35, delete "($-CH_2C=CH$)" and insert --($-CH_2C{\equiv}CH$)--.

UNITED STATES PATENT AND TRADEMARK OFFICE
CERTIFICATE OF CORRECTION

PATENT NO. : 5,480,856
DATED : January 2, 1996
INVENTOR(S) : Kofi Sam Amuti

It is certified that error appears in the above-indentified patent and that said Letters Patent is hereby corrected as shown below:

Column 14, line 49; Column 15, lines 6 and 16; Column 16, lines 10, 29 and 50; Column 17, lines 6 and 63; Column 18, lines 6, 19, 36 and 60; Column 19, lines 6, 29 and 58; Column 20, lines 6 and 26; Column 21, lines 17 and 45; Column 22, line 6; and Column 24, line 50, move "g/ha" up 1 line keeping it in the same table column as it now reside but placed immediately following the numerical values for the g/ha.

Signed and Sealed this

First Day of July, 1997

*Attest:*

*Attesting Officer*

BRUCE LEHMAN

*Commissioner of Patents and Trademarks*